United States Patent
Lee et al.

(10) Patent No.: US 10,695,390 B2
(45) Date of Patent: Jun. 30, 2020

(54) COMPOSITION FOR TREATING OR PREVENTING LIVER DISEASES, CONTAINING SICYOS ANGULATUS EXTRACT AS ACTIVE INGREDIENT

(71) Applicant: KOREA RESEARCH INSTITUTE OF BIOSCIENCE AND BIOTECHNOLOGY, Daejeon (KR)

(72) Inventors: Chul Ho Lee, Daejeon (KR); Yong-Hoon Kim, Daejeon (KR); Jung Ran Noh, Daejeon (KR); Dong Hui Choi, Daejeon (KR); Jung Hwan Hwang, Daejeon (KR); Kyoung Shim Kim, Daejeon (KR); Yun-Jung Seo, Daejeon (KR); In-Bok Lee, Daejeon (KR); Jung-Hyeon Choi, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 124 days.

(21) Appl. No.: 16/060,780

(22) PCT Filed: Dec. 9, 2016

(86) PCT No.: PCT/KR2016/014427
§ 371 (c)(1),
(2) Date: Jun. 8, 2018

(87) PCT Pub. No.: WO2017/099509
PCT Pub. Date: Jun. 15, 2017

(65) Prior Publication Data
US 2018/0360897 A1    Dec. 20, 2018

(30) Foreign Application Priority Data
Dec. 10, 2015    (KR) .................. 10-2015-0176110

(51) Int. Cl.
*A61K 36/428*    (2006.01)
*A61K 36/42*    (2006.01)
(Continued)

(52) U.S. Cl.
CPC .............. *A61K 36/42* (2013.01); *A23K 10/30* (2016.05); *A23L 33/105* (2016.08); *A61P 1/16* (2018.01); *A23V 2002/00* (2013.01)

(58) Field of Classification Search
CPC .................................................... A61K 36/428
See application file for complete search history.

(56) References Cited

FOREIGN PATENT DOCUMENTS

| KR | 10-2007-0065942 A | 6/2007 |
| KR | 10-2014-0045651 A | 4/2014 |
| KR | 10-2014-0067642 A | 6/2014 |

OTHER PUBLICATIONS

Search Report and Written Opinion issued for PCT application No. PCT/KR2016/014427 dated Apr. 10, 2017 (9 pages).
(Continued)

*Primary Examiner* — Rosanne Kosson
(74) *Attorney, Agent, or Firm* — Rothwell, Figgs, Ernst & Manbeck, P.C.

(57) ABSTRACT

The present invention relates to: a composition comprising a *Sicyos angulatus* extract or a fraction thereof as an effective ingredient for preventing, alleviating, or treating liver diseases; and a method for preventing or treating liver diseases, comprising a step of administering the composition to a subject suspected of having a liver disease.

14 Claims, 6 Drawing Sheets

(51) Int. Cl.
 *A23K 10/30* (2016.01)
 *A23L 33/105* (2016.01)
 *A61P 1/16* (2006.01)

(56) References Cited

OTHER PUBLICATIONS

Na, C. S. et al., Flavonol 3,7-diglycosides from the aerial parts of Sicyos angulatus (Cucurbitaceae) in Korea and Japan, Biochemical Systematics and Ecology, 2013, vol. 48, pp. 235-237.

Choi, So Jin et al., Screening of Korean Herbal Medicines with Inhibitory Activity on Advanced Glycation End Products (AGEs) Formation (XII), Korean Journal of Pharmacognosy, Sep. 2015, vol. 46, No. 3, pp. 250-259.

COMPOSITION FOR TREATING OR PREVENTING LIVER DISEASES, CONTAINING SICYOS ANGULATUS EXTRACT AS ACTIVE INGREDIENT

The present application is a 35 U.S.C. § 371 National Phase Entry Application from PCT/KR2016/014427, filed on Dec. 9, 2016, and designating the United States, which claims the benefits of priority to Korean Patent Application No. 10-2015-0176110, filed Dec. 10, 2016 which are incorporated herein by reference in their entirety for all purpose.

TECHNICAL FIELD

The present invention relates to a composition comprising a *Sicyos angulatus* extract or a fraction thereof as an effective ingredient for preventing, alleviating, or treating a liver disease and a method for preventing or treating a liver disease, the method comprising a step of administering the composition to a subject suspected of having a liver disease.

BACKGROUND ART

The dysfunction of the liver, which is an organ playing a core role in nutrient metabolism, causes problems with nutrient metabolism in the body. When slightly damaged, the liver can recuperate hepatocytes thereof though rest, but persons in the present-day society who are too busy to rest tend to develop liver disease. Liver diseases include fatty liver, hepatitis, liver cirrhosis, liver cancer, etc., with hepatitis being most common. Hepatitis, which is inflammation of the liver tissue, may be acute or chronic depending on the lasting period thereof and is classified into viral hepatitis, alcoholic hepatitis, and drug-induced hepatitis by causes. At present, drugs are prescribed, in combination with exercise, alcohol abstinence, diet therapy, and the like, for the treatment of hepatitis, but completely healing from hepatitis is difficult by such means. Thus, there is a continued need for a therapeutic agent for liver diseases or a hepatoprotective agent, which is effective and improved.

Medicines which are used as hepatoprotective and therapeutic agents for liver diseases become nutrients for the liver, serving to stabilize hepatocytes and activate enzymes in hepatocytes. Representative of the medicines are silymarin and biphenyldimethyl dicarboxylate (BDD) (Korea Patent Nos. 10-0090902 and 10-0577514). Silymarin is an extract from fruits of milk thistle, which is in the Compositae family and BDD can be extracted from *Schisandra chinensis*. These medicines are known to protect the liver by suppressing lipid oxidation in hepatocytes thanks to the potent antioxidant effects thereof. However, these therapeutic agents for liver diseases have a limitation in showing temporal effects rather than fundamentally ameliorating liver diseases and suffer from the disadvantage of inducing rapid actions or causing side effects upon mass or long-term administration.

Technical Problem

Leading to the present invention, thorough and intensive research into a substance effective for the treatment of liver diseases without side effects resulted in the finding that a *Sicyos angulatus* extract reduces LPS-induced inflammation, suppresses ROS generation in hepatocytes, and inhibits hepatitis and liver damage in all of hepatitis and liver damage animal models induced by concanavalin A, carbon tetrachloride, or acute alcohol administration.

SUMMARY OF THE INVENTION

Technical Solution

It is a purpose of the present invention to provide a pharmaceutical composition containing a *Sicyos angulatus* extract or a fraction thereof as an effective ingredient for preventing or treating a liver disease.

It is another purpose of the present invention to provide a food composition containing a *Sicyos angulatus* extract or a fraction thereof as an effective ingredient for preventing or alleviating a liver disease.

It is a further purpose of the present invention to provide a feed composition containing a *Sicyos angulatus* extract or a fraction thereof as an effective ingredient for preventing or alleviating a liver disease.

It is a still further purpose of the present invention to provide a method for treating or preventing a liver disease, the method comprising a step of administering the composition to a subject suspected of having a liver disease.

It is a still another purpose of the present invention to provide the use of a *Sicyos angulatus* extract or a fraction thereof in preventing or treating a liver disease.

Advantageous Effects

Found to be effective for the treatment and prevention of a liver disease by inhibiting the generation of various inflammatory cytokines and inflammatory mediators resulting from inflammatory responses, suppressing the increase of reactive oxygen species, and reducing levels of GOT (glutamyl oxaloacetic transaminase) and GPT (glutamyl pyruvate transaminase), which are indicators of liver damage, a *Sicyos angulatus* extract or a fraction thereof can be used in a composition having an outstanding prophylactic or therapeutic effect on a liver disease.

DETAILED DESCRIPTION OF THE INVENTION

Best Mode

An aspect of the present invention provides a composition comprising a *Sicyos angulatus* extract or a fraction thereof as an effective ingredient for preventing or treating a liver disease.

In the present invention, a *Sicyos angulatus* extract or a fraction thereof was found to have the effect of reducing a level of reactive oxygen species (ROS), suppressing hepatic inflammation, and protecting hepatocytes from liver damage and thus can be used in the prevention or treatment of a liver disease.

As used herein, the term "*Sicyos angulatus*" refers to an annual or biennial vine in the gourd family. The plant is known to have herbicidal activity and antibacterial activity, but had not yet been known for a preventive or therapeutic effect on a liver disease until the present inventors first found the effect.

As used herein, the term "extract" is intended to encompass the extract itself and all possible formulations of the extract, such as extract liquid obtained through extraction of *Sicyos angulatus*, a diluent or concentrate of the extract liquid, a dehydrate obtained by drying the extract liquid, a crude or filtrate of the extract liquid, or a combination thereof.

In the present invention, the *Sicyos angulatus* extract may be obtained by washing, drying, and then pulverizing *Sicyos angulatus*; and extracting the pulverized *Sicyos angulatus* with a solvent selected from the group consisting of water, C1-C4 alcohol, and a combination thereof. Particularly, the *Sicyos angulatus* extract may be obtained by extraction with methanol, ethanol, propanol, or butanol, and more particularly with methanol, but without limitations thereto.

No particular limitations are imparted to extraction methods, and extraction may be made at room temperature or by mild heating under the condition in which effective ingredients are minimally destroyed or not harmed at all. In greater detail, the *Sicyos angulatus* extract is obtained as follows. Dry *Sicyos angulatus* may be extracted with a volume of a polar solvent, such as water, a C1-C4 alcohol, e.g., methanol, ethanol, propanol, and butanol, or a mixed solvent thereof having a mixture ratio of 1:0.1 to 1:10, wherein the volume corresponds to a weight about 2- to 20-fold, in detail, 3- to 5-fold greater than the weight of dry *Sicyos angulatus*. The extraction temperature may be 1 to 100° C. and particularly 25° C. The period of extraction may range from about one hour to ten days and particularly from two to fifty hours. Examples of the extraction method include agitation extraction, hot-water extraction, cold-precipitation extraction, flux cooling extraction, ultrasonic extraction, and a combination thereof, but are not limited thereto. In an exemplary Example of the present invention, a cycle of ultrasonication for 15 min and then stagnation at room temperature for 2 hours was repeated ten times per day to give an extract which was then filtered, concentrated, and lyophilized to afford a *Sicyos angulatus* extract.

The *Sicyos angulatus* extract may be obtained from natural, hybrid, or variant plants and extraction is possible from a plant tissue culture.

As used herein, the term "fraction" refers to a result obtained by isolating a specific ingredient or a specific ingredient group from a mixture of various ingredients through fractioning.

No particular limitations are imparted to the fractioning method of obtaining the fraction. So long as it is typically used in the art, any method may be employed. In a non-limiting example of the fractioning method, an extract obtained by subjecting *Sicyos angulatus* to extraction may be treated with a certain solvent to give a fraction.

Kinds of the fraction solvents are not particularly limited, and any solvent that is known in the art may be used. Non-limiting examples of the fraction solvent include: polar solvents such as water, alcohols, etc.; and non-polar solvents such as hexane, ethyl acetate, acetone, chloroform, etc. The solvents may be used alone or in combination of two or more thereof.

As used herein, the term "prevention" or "preventing" means all actions that inhibit or delay the onset of a liver disease by administration of a *Sicyos angulatus* extract, a fraction thereof, or a composition according to the present invention. As used herein, the term "treatment" or "treating" means all actions that are intended to ameliorate or beneficially change a symptom associated with the disease by administering a *Sicyos angulatus* extract, a fraction thereof, or a composition according to the present invention.

The term "liver disease", as used herein, refers to the inability of the liver to normally perform metabolism because of a failure in at least one of various functions that the liver performs. The most prevalent among liver diseases is hepatitis, which may be divided into acute hepatitis and chronic hepatitis. Generally, acute hepatitis is easy to treat and accounts for benign cases. In terms of causes, acute hepatitis includes viral hepatitis, alcoholic hepatitis, and toxic hepatitis. Any liver disease that can be treated by means of the *Sicyos angulatus* extract or a fraction thereof may fall within the scope of the present invention, without limitations thereto. Examples of the liver diseases include hepatitis, toxic hepatopathy, cholestasis, fatty liver, liver cirrhosis, hepatic ischemia, alcoholic liver diseases, liver abscess, hepatic encephalopathy, atrophy of the liver, and liver cancer. In the present invention, a *Sicyos angulatus* extract is identified to have preventive and therapeutic effects on liver diseases.

Figure 1:
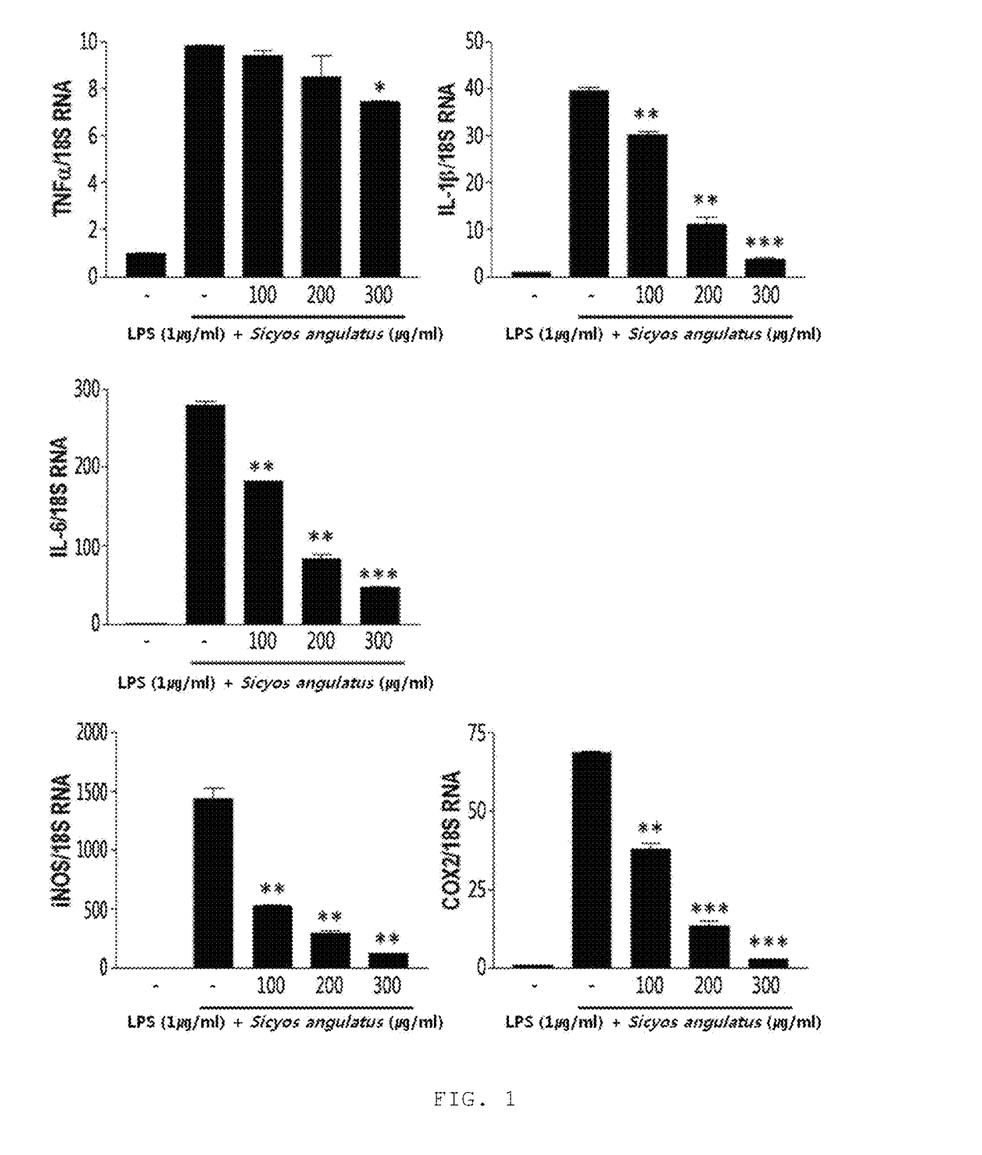
FIG. 1 shows graphs depicting gene expressions of inflammation-related markers in the macrophage cell line (Raw264.7 cells) which were treated with lipopolysaccharide (LPS) to induce an inflammatory response and optionally with a *Sicyos angulatus* extract (*: $p<0.05$, : $p<0.01$, *: $p<0.001$)
Figure 2A:
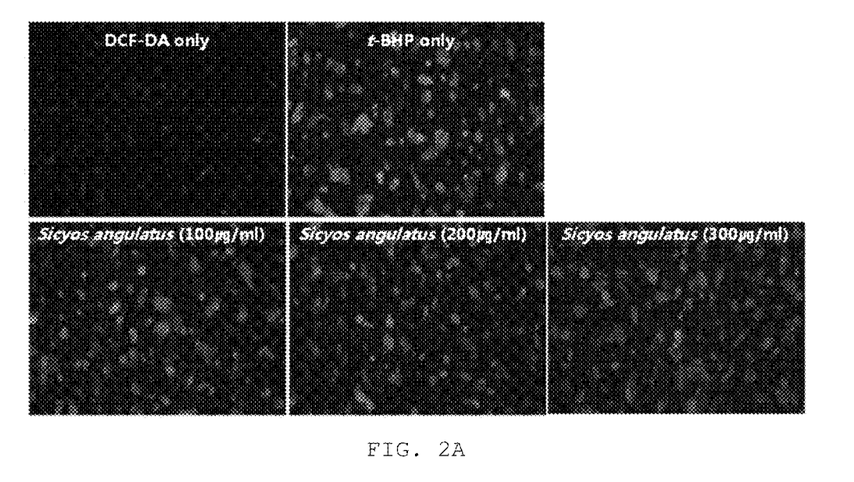
FIG. 2A shows staining images accounting for generation levels of ROS depending on treatment with a *Sicyos angulatus* extract.
Figure 2B:
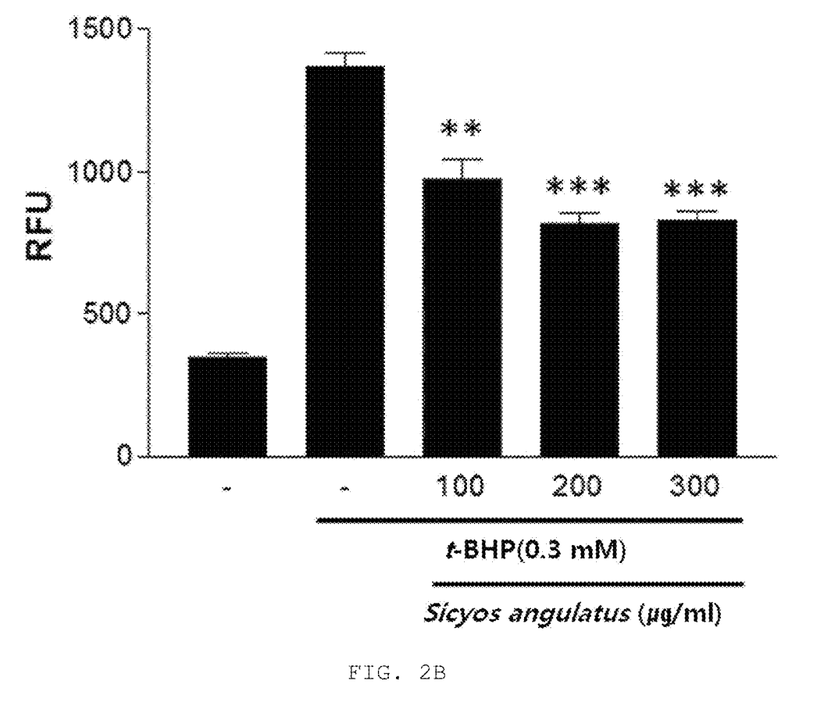
FIG. 2B is a graph quantitatively illustrating the generation of ROS depending on treatment with a *Sicyos angulatus* extract (: $p<0.01$, *: $p<0.001$).
Figure 3A:
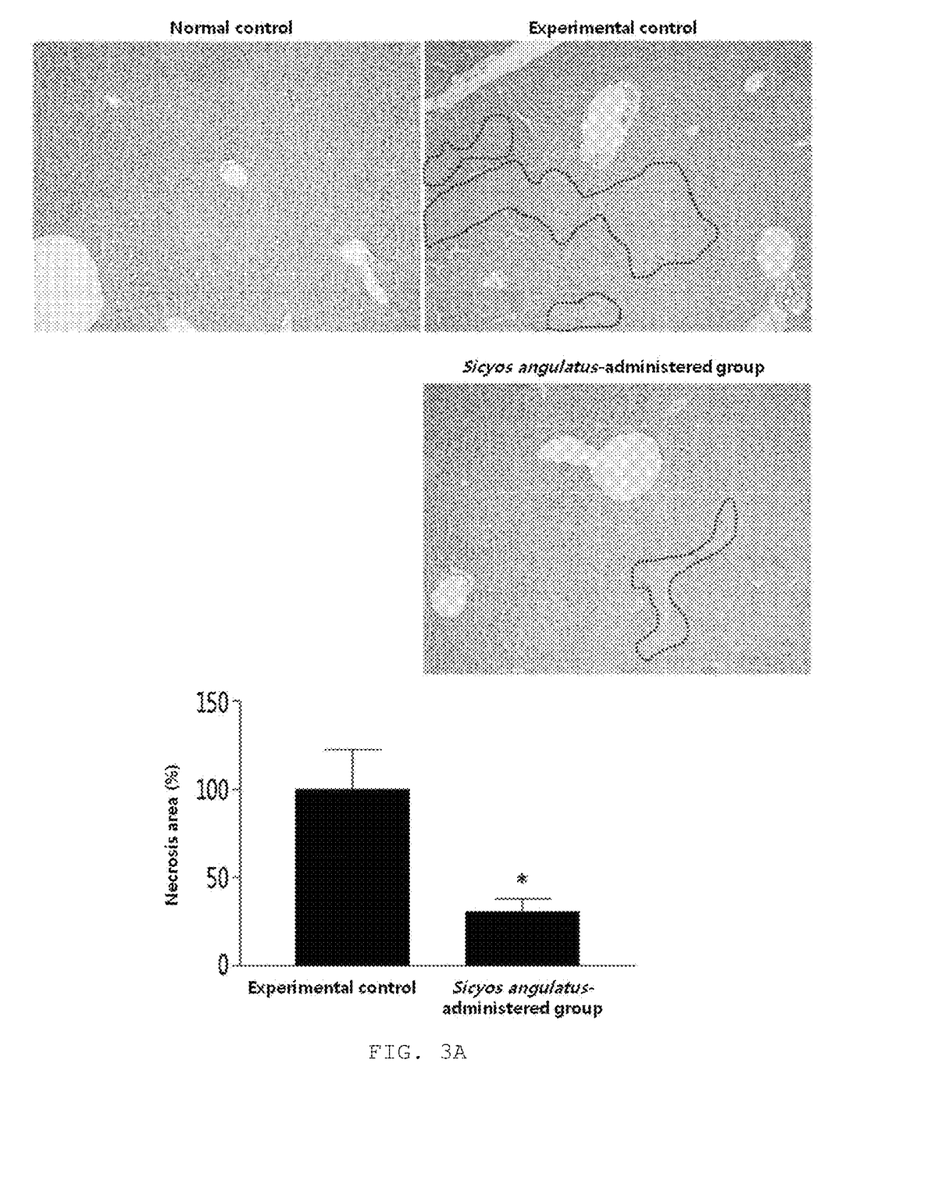
FIG. 3A shows necrotic areas in liver tissues of mouse models in which hepatitis has been induced by concanavalin A (ConA), depending on administration with a *Sicyos angulatus* extract (*: $p<0.05$).
Figure 3B:
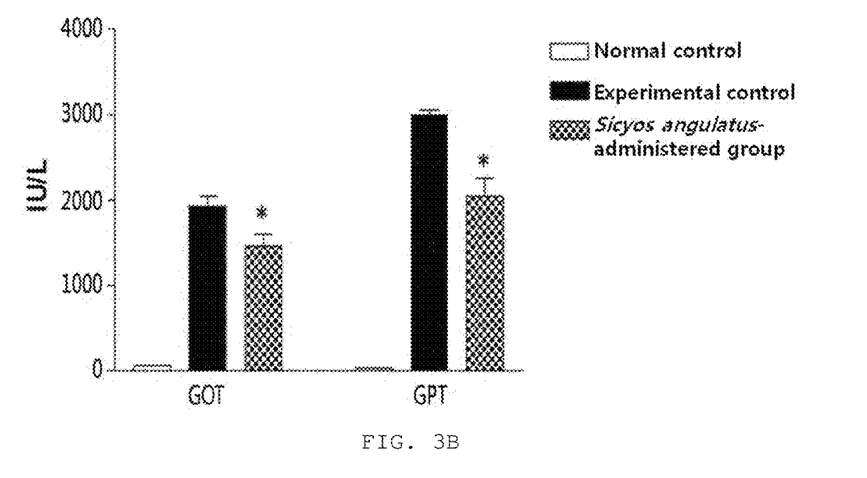
FIG. 3B is a graph illustrating levels of the liver damage indicators GOT and GPT in mouse models having hepatitis induced by concanavalin A (ConA), depending on administration with a *Sicyos angulatus* extract (*: $p<0.05$).
Figure 4:
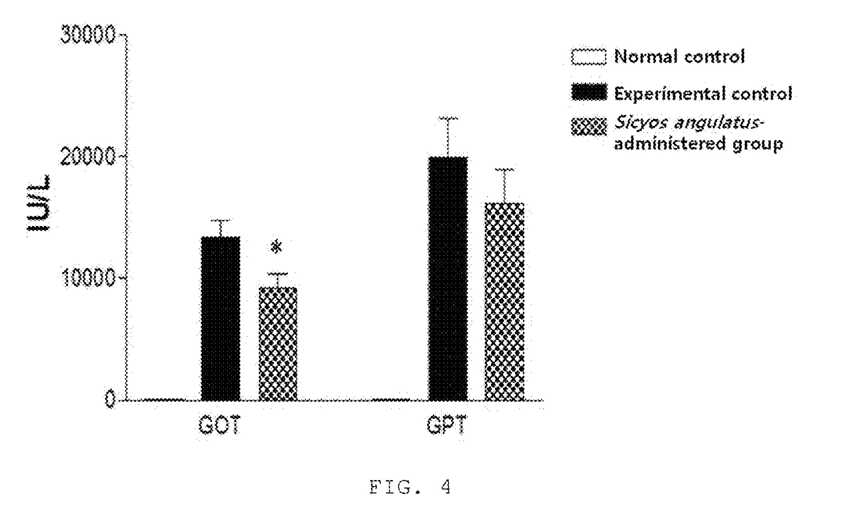
FIG. 4 is a graph illustrating levels of the liver damage indicators GOT and GPT in mouse models having liver damage induced by carbon tetrachloride, depending on administration with a *Sicyos angulatus* extract (*: $p<0.05$).
Figure 5:
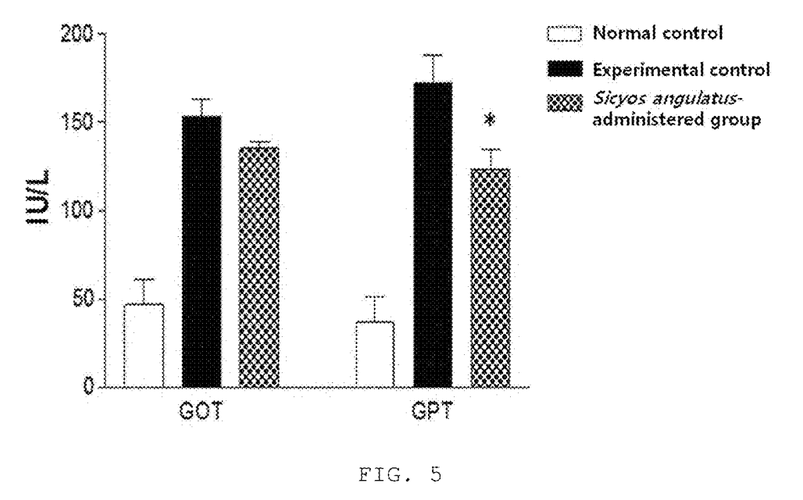
FIG. 5 is a graph illustrating levels of the liver damage indicators GOT and GPT in mouse models having liver damage induced by acute alcohol administration, depending on administration with a *Sicyos angulatus* extract (*: $p<0.05$).

In an exemplary embodiment of the present invention, the mouse macrophage cell line Raw264.7 in which inflammation was induced by LPS after treatment with a *Sicyos angulatus* extract was observed to show restrained gene expression of inflammatory cytokines (TNFα, IL-6, and IL-1β) and inflammatory mediators (iNOS and COX2) (FIG. 1). In addition, the treatment of the liver cancer cell line HepG2 with a *Sicyos angulatus* was found to reduce the generation of reactive oxygen species resulting from the oxidative stress induced by t-BHP (tert-butylhydroperoxide) (FIG. 2). Further, all mouse models in which acute liver damage or hepatitis was induced by concanavalin A (ConA), carbon tetrachloride, or alcohol were observed to have reduced levels of glutamyl oxaloacetic transaminase (GOT) and glutamyl pyruvate transaminase (GPT), which are indicators of liver damage and to show restraint hepatic necrosis in actual liver tissues when administered orally with a *Sicyos angulatus* extract (FIGS. 3 to 5).

The data obtained indicates that the composition comprising a *Sicyos angulatus* extract or a fraction thereof according to the present invention has an excellent effect on the prophylaxis and therapy of a liver disease.

In the present invention, the liver disease may be a fatty liver. In particular, the fatty liver may be an alcoholic or a non-alcoholic fatty liver. As used herein, "alcoholic fatty liver" means a liver disease that occurs with excessive alcohol intake. Excessive alcohol intake promotes lipogenesis and interferes with normal energy metabolism in the liver. As used herein, the term "non-alcoholic fatty liver" means a metabolic syndrome associated with the fat accumulation, caused by factors other than alcohol, in liver cells. A concrete example may be a fatty liver induced by excessive calorie intake. Having prophylactic and therapeutic effects on alcoholic and non-alcoholic fatty livers, a *Sicyos angulatus* extract or a fraction thereof according to the present invention may be used in a pharmaceutical composition for preventing and treating alcoholic fatty liver and non-alcoholic fatty liver.

Figure 6:
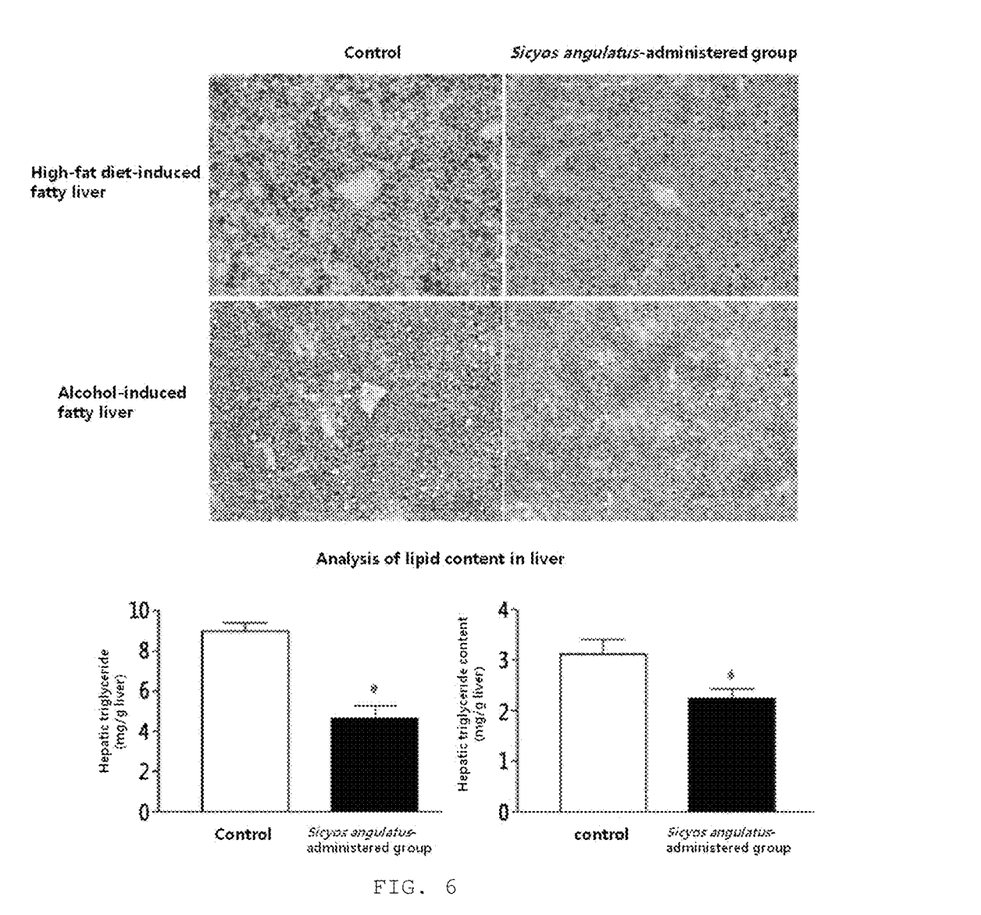
FIG. 6 shows the development of fatty liver and levels of triglyceride in mouse models having fatty liver induced by a high-fat diet or alcohol, depending on administration with a *Sicyos angulatus* extract (*: $p<0.05$).

In an exemplary embodiment of the present invention, animal models having high-fat diet- or alcohol-induced fatty liver were orally administered with a *Sicyos angulatus* extract and then, liver tissue samples were taken therefrom, observed for the formation of fatty liver, and analyzed for triglyceride levels. Reduced levels of fatty liver formation and triglyceride were detected in experimental groups administered with a *Sicyos angulatus* extract, compared to a control (FIG. 6).

The composition for prevention or treatment of a liver disease according to the present invention may be administered in the form of a pharmaceutically acceptable salt and may be used alone or in combination with a different pharmaceutically active compound as well as in an appropriate set.

The composition for prevention or treatment of a liver disease according to the present invention may further comprise a pharmaceutically acceptable carrier.

The composition for prevention or treatment of a liver disease according to the present invention may be prepared into a pharmaceutical formulation for providing a rapid, sustained, or delayed release of an active ingredient after administration to mammals, using a method well known in the art. In preparing a formulation, the active ingredient may be preferably mixed or diluted with a carrier or mounted in a vessel form of a carrier.

Accordingly, the composition for prevention or treatment of a liver disease according to the present invention may be formulated into oral dosage forms, such as powders, granules, tablets, capsules, suspensions, emulsions, syrups, aerosols, and the like, external use agents, suppositories, and sterile injection solutions, and may further comprise suitable carriers, excipients, and diluents that are typically used.

Examples of the carrier available in the composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oils, but are not limited thereto. For formulation, a typically used diluent or excipient such as a filler, a thickener, a binder, a humectant, a disintegrant, a surfactant, etc. may be employed.

Solid preparations for oral dosage include tablets, pills, powders, granules, capsules, and the like and are formulated by admixing at least one excipient, such as starch, calcium carbonate, sucrose, lactose, gelatin, etc. with the active ingredient. In addition, a lubricant such as magnesium stearate, talc, etc. may be used in addition to a simple excipient.

Among liquid preparations intended for oral administration are suspensions, internal use solutions, emulsions, syrups, and the like. Plus a simple diluent, such as water or liquid paraffin, various excipients, such as humectants, sweeteners, aromatics, preservatives, and the like may be contained in the liquid preparations.

Also, the pharmaceutical composition of the present invention may be in a parenteral dosage form such as sterile aqueous solutions, non-aqueous solvents, suspensions, emulsions, lyophilizates, suppositories, and the like. Propylene glycol, polyethylene glycol, vegetable oils such as olive oil, and injectable esters such as ethyl oleate may be suitable for the non-aqueous solvents and suspensions. The basic materials of suppositories include Witepsol, Macrogol, Tween 61, cacao butter, laurin butter, glycerogelatin.

The pharmaceutical composition of the present invention may be administered as an individual therapeutic agent alone or in combination with other therapeutics. The co-administration of the pharmaceutical composition of the present invention with conventional therapeutics may be carried out sequentially or simultaneously. Single or multiple dosages are possible. It is important to use the composition in the minimum possible amount sufficient to obtain the greatest therapeutic effect without side effects in consideration of all the factors, which could easily be determined by a person skilled in the art.

As used therein, the term "administration" means introducing the pharmaceutical composition of the present invention into a patient by any appropriate method. The composition of the present invention may be administered by any general oral or parenteral route as long as it can reach a target tissue.

Without particular limitations thereto, any administration mode may be available for the pharmaceutical composition according to the present invention as long as it is typically used in the art. Non-limiting examples of the administration mode include oral or parenteral administration modes. The pharmaceutical composition according to the present invention may be prepared into various dosage forms, depending on desired administration modes.

As for administration frequency, the composition of the present invention may be administered once a day or many times a day at divided doses, but the administration frequency is not particularly limited thereto.

The composition comprising a *Sicyos angulatus* extract or a fraction thereof in accordance with the present invention may be administered such that the *Sicyos angulatus* extract or a fraction thereof has a daily dose of from 10 to 1,000 mg/kg and particularly from 10 to 600 mg/kg and the composition of the present invention may be administered in a single dosage or may be divided into multiple dosages per day.

Another aspect of the present invention provides a method for preventing or treating a liver disease, the method comprising a step of administering the composition to a subject suspected of having a liver disease, for example, to a subject suspected of having a liver disease, except for a human being.

The *Sicyos angulatus* extract and the liver disease are as described above.

As used herein, the term "subject" refers to all animals, including humans, which have undergone or are likely to undergo the onset of a liver disease. The animals include, but are not limited to, humans as well as mammals such as cows, horses, sheep, pigs, goats, camels, antelopes, dogs, cats, etc., in need of treating symptoms similar to liver diseases.

The preventing or treating method of the present invention may comprise a step of administering the composition in a pharmaceutically effective amount to a subject in which a liver disease has occurred or is likely to occur.

A further aspect of the present invention provides a food composition comprising a *Sicyos angulatus* extract or a fraction thereof as an effective ingredient for preventing or alleviating a liver disease.

Allowed for ingestion thereof in a daily life, the food composition of the present invention is expected to be very effective for preventing or alleviating a liver disease.

The term "alleviation" or "alleviating", as used herein, refers to all actions that ameliorate or beneficially change symptoms associated with a liver disease by administering the composition of the present invention.

The food composition for preventing or alleviating a liver disease in accordance with the present invention may be in the form of a pill, a powder, a granule, a precipitate, a tablet, a capsule, or liquid. Among the foods to which the composition of the present invention can be added are various foods, for example, beverages, gum, teas, vitamin complexes, and health aid foods.

No particular limitations are imparted to ingredients in the food composition for preventing or alleviating a liver disease other than the indispensable ingredients inclusive of the composition containing the *Sicyos angulatus* extract for preventing and treating a liver disease, an effective ingredient thereof, or a biologically acceptable salt thereof. Like typical foods, the food composition may contain various herb extracts, food aid additives, or natural carbohydrates.

As used herein, the term "biologically acceptable salt" refers to a salt that is biologically acceptable and which, when administered to an organism, exhibits an intended effect of an administered compound without causing an allergic reaction or any symptoms similar thereto such as stomach disorders and dizziness.

In addition, as mentioned above, a food aid additive may be additionally added and may include a typical one used in the art, such as a flavorant, a savoring agent, a colorant, a filter, and a stabilizer.

Examples of the natural carbohydrate include typical sugars such as monosaccharides, e.g., glucose, fructose, etc.; disaccharides, e.g., maltose, sucrose, etc.; and polysaccharides, e.g., dextrin, cyclodextrin, etc., and sugar alcohols, e.g., xylitol, sorbitol, erythritol, etc. In addition to the foregoing, a flavorant such as a natural flavorant (e.g., rebaudioside A, glycyrrhizin, etc.) and a synthetic flavorant (e.g., saccharin, aspartame, etc.) may be advantageously used.

Furthermore, the composition for prevention or alleviation of a liver disease according to the present invention may include various nutrients, vitamins, minerals (electrolytes), savoring agents such as synthetic and natural savoring agents, colorants and weighing agents (cheese, chocolate, etc.), pectic acid and salts thereof, alginic acid and salts thereof, organic acids, protective colloids, thickeners, pH adjusters, stabilizers, preservatives, glycerin, alcohols, and carbonating agents for soda pops. In addition, the composition may contain natural fruit juice and fruit fresh for preparation of fruit juice beverages and vegetable beverages. These ingredients may be used independently or in combination.

In the present invention, the health aid food includes a health functional food and a health food.

The term "health functional food" is the same term as a food for special health use (FOSHU) and refers to a food which is processed to effectively exert a body-regulating function in addition to nutrient supply, thus having high medicinal and medical effects. Here, "function(al)" means pertaining to controlling nutrients for structures and functions of the human body or obtaining beneficial effects in hygienic use such as in physiological functions. The food of the present invention can be prepared using a method typically used in the art. Materials and ingredients typically used in the art may be used for the preparation of the food. The food may be prepared into any formulation that is regarded as a food, without limitations. The food composition of the present invention may be prepared into various formulations and has an advantage over general drugs in that the food composition is free of side effects which might occur upon long-term intake of drugs because it is based on food materials. Further, the food of the present invention is of high portability such that it can be ingested as an aid for promoting the prophylactic or alleviative effect on liver diseases.

Yet another aspect of the present invention provides a feed composition comprising a *Sicyos angulatus* extract or a fraction thereof as an effective ingredient for preventing or alleviating a liver disease.

The *Sicyos angulatus* extract and the liver disease are as described above.

The feed composition may comprise a feed additive. The feed additive of the present invention corresponds to an auxiliary feed under the Control of Livestock and Fish Feed Act.

As used herein, the term "feed" refers to any natural or artificial diet, a meal, or its components for animals to eat, ingest, and digest, or the like.

Without particular limitations to kinds thereof, typical feeds used in the art may be available. Non-limiting examples of the feed include: vegetable feeds such as crops, root plants, food-processing by-products, algae, fibroid materials, pharmaceutical by-products, fat and oils, starches, meals or crop by-products; and animal feeds such as proteins, inorganics, fat and oils, minerals, single-cell proteins, animal planktons or foods. These feeds may be used individually or in a mixture of at least two thereof.

A still further aspect of the present invention provides the use of a *Sicyos angulatus* extract or a fraction thereof in preventing or treating a liver disease.

Found to be effective for the treatment and prevention of a liver disease by inhibiting the generation of various inflammatory cytokines and inflammatory mediators resulting from inflammatory responses, suppressing the increase of reactive oxygen species, and reducing levels of GOT (glutamyl oxaloacetic transaminase) and GPT (glutamyl pyruvate transaminase), which are indicators of liver damage, a *Sicyos angulatus* extract or a fraction thereof was identified to have use in preventing or treating a liver disease in the present invention.

MODE FOR CARRYING OUT THE INVENTION

A better understanding of the present invention may be obtained through the following examples which are set forth to illustrate, but are not to be construed as limiting the present invention.

Example 1: Preparation of *Sicyos Angulatus* Extract

*Sicyos angulatus* was dried and pulverized, followed by ten cycles of sonication of the pulverized powder for 15 min in methanol and then leaving the solution at room temperature for 2 hours to give an extract solution. This extract solution was filtered, concentrated, and frozen in a deep freezer before drying in a freeze drier. The *Sicyos angulatus* extract thus obtained was dissolved in DMSO for use in experiments with liver cell lines and macrophage cell lines and in 0.5% carboxymethyl cellulose (CMC) for use in animal experiments.

Example 2: Assay of *Sicyos angulatus* Extract for Anti-Inflammatory Efficacy in Macrophage The macrophage cell line Raw264.7 was treated with 100, 200, or 300 μg/ml of a *Sicyos angulatus* extract, together with 1 μg/ml of lipopolysaccharide (LPS) to induce an inflammatory response. After culturing the cells for 24 hours, RNA was isolated from the cells and analyzed for gene expression of inflammation-related cytokines (TNFα, IL-6, and IL-1β) and inflammation mediators (iNOS and COX2) (FIG. 1).

As a result, the *Sicyos angulatus* extract was observed to reduce an LPS-induced inflammatory response in a dose-dependent manner. From the result, it was identified that the *Sicyos angulatus* extract has an inhibitory effect on inflammatory responses.

Example 3: Assay of *Sicyos angulatus* Extract for Inhibitory Potential Against Reactive Oxygen Species The liver cancer cell line HepG2 was incubated with 100, 200, or 300 μg/ml of a *Sicyos angulatus* extract for 3 hours, followed by treatment with 300 μM t-BHP (tert-butylhydroperoxide) to induce oxidative stress. One hour later, the cells were incubated for an additional 60 min in a fresh medium containing 20 μM DCF-DA (2',7'-Dichlorofluorescein diacetate) so as to measure intracellularly generated reactive oxygen species (ROS). The ROS generated was analyzed by fluorescence microscopy.

Treatment with the *Sicyos angulatus* extract was observed to reduce t-BHP-induced ROS generation in hepatocytes by 40% or greater (FIGS. 2A and 2B). The result indicates that the *Sicyos angulatus* extract has protective activity against oxidative stress.

Example 4: Assay of Administration Effect of *Sicyos angulatus* Extract in Animal Model with Concanavalin A-Induced Non-Fatty Hepatitis The effect of a *Sicyos angulatus* extract on concanavalin A (ConA)-induced hepatitis without fatty liver was evaluated. To this end, male C57BL/6 mice eight weeks old were orally administered once with a 300 mg/kg suspension of a *Sicyos angulatus* extract in 0.5% CMC. After 30 min of the *Sicyos angulatus* extract administration, a solution of ConA in PBS was injected at a concentration of 15 ml/kg via a tail vein. Six hours later, blood and liver tissues were sampled from the mice. The liver tissue samples were fixed with 10% neutral formalin for 24 hours or longer, dehydrated with ethanol, embedded into paraffin blocks, and sectioned into 4 μm-thick tissue slices by a microtome. The slices on slides were stained with hematoxylin and eosin and observed under an optical microscope to analyze the necrosis of hepatocytes in which acute hepatitis had been induced by ConA.

Calculation was made of necrotic areas in liver tissues. Necrosis caused by acute hepatitis was widely observed across the liver tissues in the experimental control group while only a significantly reduced area of the liver tissue in a *Sicyos angulatus* extract-administered group suffered from necrosis (FIG. 3A).

In order to evaluate the preventive effect of a *Sicyos angulatus* extract on hepatitis in mouse models with ConA-induced hepatitis, glutamyl oxaloacetic transaminase (GOT) and glutamyl pyruvic transaminase (GPT), which are both representative indictors of liver damage, were analyzed. In this regard, a blood sample was taken from the retro-orbital sinus of each animal, using a heparinized capillary tube and centrifuged at 10,000 rpm for 10 min. The supernatant plasma thus obtained was analyzed, using an automatic blood analyzer (Hitachi 7150, Japan).

Blood GOT and GPT levels were measured to be 1930±105 IU/L and 2822±172 IU/L in the experimental control group and 1462±134 IU/L and 2042±204 IU/L in a *Sicyos angulatus* extract-administered group, respectively. Consequently, GOT and GPT levels were significantly reduced in the administered group, compared to the experimental control group (FIG. 3B).

The analysis results indicate that the *Sicyos angulatus* extract effectively suppresses concanavalin A-induced hepatitis, exhibiting hepatoprotective activity.

Example 5: Assay of Administration Effect of *Sicyos angulatus* Extract in Animal Model with Carbon Tetrachloride-Induced Liver Damage A suspension of a *Sicyos angulatus* extract in 0.5% CMC was orally administered once at a dose of 1 g/kg to male C57BL/6 mice eight weeks old. Thirty minutes after administration of the *Sicyos angulatus* extract, a mixture of equal volumes of carbon tetrachloride and corn oil (1:1 v/v) was intraperitoneally injected at a dose of 1 ml/kg, followed by starving the mice for 24 hours before blood and liver tissues were sampled from the mice. During experiments, all mice were given ad libitum access to water. Mice were maintained in an SPF-barrier facility, the condition of which was controlled for temperature at 22±2° C. and humidity at 55±10%, with a 12-h light/dark cycle.

Blood GOT and GPT levels were measured to be 13335±1455 IU/L and 19890±3174 IU/L in an experimental control group and 9200±1164 IU/L and 16168±2710 IU/L in the *Sicyos angulatus* extract-administered group, respectively. The administration of the *Sicyos angulatus* extract reduced both GOT and GPT levels, with a particularly significant reduction in GOT level (FIG. 4). The analysis results indicate that the *Sicyos angulatus* extract can effectively suppress carbon tetrachloride-induced hepatocyte damage, having hepatoprotective activity.

Example 6: Assay of Administration Effect of *Sicyos angulatus* Extract in Animal Model with Acute Alcoholic Liver Damage Induced Therein A suspension of a *Sicyos angulatus* extract in 0.5% CMC was orally administered once at a dose of 600 mg/kg to male C57BL/6 mice eight weeks old. Thirty minutes after administration of the *Sicyos angulatus* extract, a 25.3% alcohol dilution was orally administered at a dose of 6 g/kg to the mice. Twelve hours later, blood and liver tissues were taken from the mice.

Blood GOT and GPT levels were measured to be 153±10.5 IU/L and 172±15.6 IU/L in the experimental control group and 135±4.2 IU/L and 123±10.8 IU/L in the *Sicyos angulatus* extract-administered group, respectively.

Both GOT and GPT levels were reduced in the administered group (FIG. 5). The analysis results indicate that the *Sicyos angulatus* extract effectively suppresses acute alcoholic hepatocyte damage, having hepatoprotective activity.

Taken together, the data obtained above show that the *Sicyos angulatus* extract of the present invention reduces LPS-induced inflammatory responses and suppresses ROS generation in hepatocytes and hepatitis and liver damage in animal models in which hepatitis or liver damage has been induced by concanavalin A, carbon tetrachloride, or acute alcohol administration, suggesting that the *Sicyos angulatus* extract of the present invention or a fraction thereof has very outstanding effects on the prevention, alleviation, or treatment of a liver disease.

Example 7: Assay of Administration Effect of *Sicyos angulatus* Extract in Animal Model with High-Fat Diet- or Alcohol-induced Fatty Liver Male C57B/6 mice eight weeks old were induced to have obesity, hyperlipidemia, and a fatty liver by supplying a high-fat diet for eight weeks while a *Sicyos angulatus* extract was additionally administered to the experimental group at a dose of 300 mg/kg once a day via an oral route. The experiment was stopped, eight weeks later, and liver tissues were taken, stained for lipids, and analyzed for a triglyceride level therein.

Briefly, liver tissues from each mouse were prepared into frozen sections which were then subjected to Oil red O (ORD) staining to observe the development of fatty liver. Using a triglyceride measurement kit, levels of triglyceride in liver tissues were analyzed.

In addition, male C57B/6 mice the same weeks old were injected with alcohol for two weeks to induce a fatty liver and analyzed for fatty liver in the same manner as in the high-fat diet models.

As a result, the fatty liver which was stained red was remarkably reduced in the experimental *Sicyos angulatus* extract-administered group, compared to the control. In addition, the triglyceride content in liver tissues was also significantly reduced in the models administered with the *Sicyos angulatus* extract irrespective of whether it was fed with a high-fat diet or alcohol (FIG. 6).

Taken together, the data suggests that the *Sicyos angulatus* extract of the present invention or a fraction thereof has prophylactic, ameliorative, or therapeutic effects on high-fat diet- or alcohol-induced fatty acid as well as concanavalin A, carbon tetrachloride or acute alcohol-induced hepatitis or liver damage.

Example 8: Statistics

All values were expressed in mean±standard error (S.E.M). For significance of the difference between the mean values, the significance level was set at 0.05. Statistic data was analyzed by Student's t-test.

While the present invention has been described with reference to the particular illustrative embodiments, it will be understood by those skilled in the art to which the present invention pertains that the present invention may be embodied in other specific forms without departing from the technical spirit or essential characteristics of the present invention. Therefore, the embodiments described above are considered to be illustrative in all respects and not restrictive. Furthermore, the scope of the present invention should be defined by the appended claims rather than the detailed description, and it should be understood that all modifications or variations derived from the meanings and scope of the present invention and equivalents thereof are included in the scope of the present invention.

INDUSTRIAL APPLICABILITY

In the present invention, it is found that a *Sicyos angulatus* extract is effective for the therapy and prophylaxis of liver diseases by suppressing the generation of various inflammatory cytokines and inflammation mediators resulting from inflammatory responses, the development of reactive oxygen species, and the level of glutamyl oxaloacetic transaminase (GOT) and glutamyl pyruvate transaminase (GPT), which are both indicators of liver damage and that the *Sicyos angulatus* extract or a fraction thereof can be thus used in a composition having excellent preventive and therapeutic effects on liver diseases. Therefore, the present invention is industrially applicable.

The invention claimed is:

1. A method for treating a liver disease in a subject in need thereof, comprising administering to the subject an effective amount of a *Sicyos angulatus* extract or a fraction thereof.

2. The method of claim 1, wherein the extract is obtained with a solvent selected from water, C1-C4 alcohols, and a combination thereof.

3. The method of claim 2, wherein the solvent is selected from the group consisting of methanol, ethanol, propanol, and butanol.

4. The method of claim 2, wherein the solvent is a combination of water and at least one alcohol selected from methanol, ethanol, propanol and butanol.

5. The method of claim 1, wherein the fraction is obtained by fractioning the *Sicyos angulatus* extract with a solvent selected from water, alcohol, hexane, ethyl acetate, acetone, chloroform, and a combination thereof.

6. The method of claim 1, wherein the liver disease is selected from the group consisting of hepatitis, toxic hepatopathy, cholestasis, fatty liver, liver cirrhosis, hepatic ischemia, alcoholic liver diseases, liver abscess, hepatic encephalopathy, atrophy of the liver, and liver cancer.

7. The method of claim 6, wherein the liver disease is fatty liver.

8. The method of claim 1, wherein the method inhibits a blood level of blood glutamyl oxaloacetic transaminase (GOT) or glutamyl pyruvic transaminase (GPT) from increasing in the subject.

9. The method of claim 1, wherein the method inhibits a reactive oxygen species level in hepatocytes or necrosis of hepatocytes from increasing in the subject.

10. The method of claim 1, wherein the subject is an animal.

11. The method of claim 1, wherein the effective amount of the *Sicyos angulatus* extract or a fraction thereof is contained in a pharmaceutical composition together with a pharmaceutically acceptable carrier.

12. The method of claim 1, wherein the effective amount of the *Sicyos angulatus* extract or a fraction thereof is contained in a food composition together with an herb extract, food aid or natural carbohydrate.

13. The method of claim 1, wherein the effective amount of the *Sicyos angulatus* extract or a fraction thereof is contained in a feed composition together with a feed additive.

14. The method of claim 10, wherein the animal is a human.

* * * * *